(12) United States Patent
Takeuchi et al.

(10) Patent No.: US 6,893,406 B2
(45) Date of Patent: May 17, 2005

(54) MASTICATION MONITORING DEVICE

(75) Inventors: Tsunehiko Takeuchi, Hamamatsu (JP); Takehiro Kurono, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 117 days.

(21) Appl. No.: 10/628,476

(22) Filed: Jul. 29, 2003

(65) Prior Publication Data

US 2004/0073142 A1 Apr. 15, 2004

(30) Foreign Application Priority Data

Jul. 30, 2002 (JP) .................................... P2002-221628

(51) Int. Cl.[7] ................................................ A61B 5/11
(52) U.S. Cl. .................................... 600/590; 73/379.02
(58) Field of Search .............................. 600/310, 322, 600/323, 340, 344, 587, 590, 595; 73/379.01, 379.02

(56) References Cited

U.S. PATENT DOCUMENTS

| | | | | |
|---|---|---|---|---|
| 4,355,645 A | * | 10/1982 | Mitani et al. | 600/590 |
| 4,859,181 A | * | 8/1989 | Neumeyer | 600/590 |
| 5,067,488 A | * | 11/1991 | Fukada et al. | 600/590 |
| 6,579,249 B2 | * | 6/2003 | Kato et al. | 600/590 |

FOREIGN PATENT DOCUMENTS

| | | |
|---|---|---|
| JP | 7-171136 | 7/1995 |
| JP | 11-123185 | 5/1999 |
| JP | 11-206740 | 8/1999 |
| JP | 2001-178706 | 7/2001 |
| JP | 2002-172103 | 6/2002 |
| JP | 2002-253520 | 9/2002 |

* cited by examiner

*Primary Examiner*—Eric F. Winakur
(74) *Attorney, Agent, or Firm*—Morgan, Lewis & Bockius LLP

(57) ABSTRACT

A mastication monitoring device 1 is provided with a probe 2 which is attached to a cheek in order to detect the concentration of reduced hemoglobin in the masticatory muscles. A photodetector 22 of the probe 2 detects light scattered in the masticatory muscles and delivers a signal of the amount of light received to a signal processing unit 3. The signal processing unit 3 computes the reduced hemoglobin concentrations (time-series changes) from the signals of the amount of light received, and further computes outputs S (time-series changes) corresponding to the time-series changes in the reduced hemoglobin concentrations. A mastication iteration counting unit 41 detects peaks in periodical changes of Sd which is the difference between the output S and the moving average value Sma of the output S and counts the peaks in periodical changes of Sd as the mastication iterations.

8 Claims, 14 Drawing Sheets

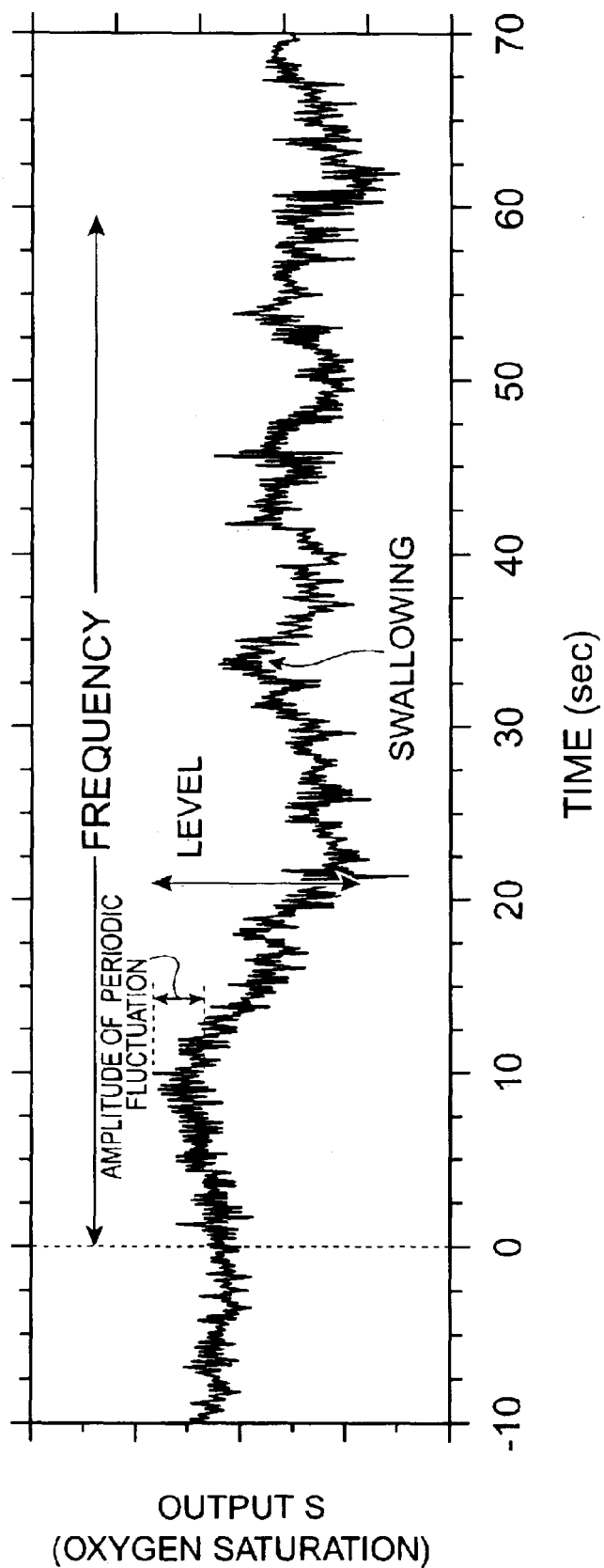

MASTICATION MONITORING DEVICE

BACKGROUND OF THE INVENTION

1. Field of the Invention

The present invention relates to a mastication monitoring device.

2. Related Background Art

It has been desired to realize a mastication monitoring device which can detect a state of mastication by a subject to be measured and provide information thereof in order to provide assistance for tutoring proper mastication, training mastication for prevention of dementia and the like. Conventional mastication monitoring devices include, for example, a device which measures the mastication iterations in response to a pressure change in the device corresponding to a movement of the skin upon masticating as disclosed in Japanese Patent Application Laid-Open No. Hei-11-206740, a device which measures the mastication iterations in response to noises generated at the time of mastication as disclosed in Japanese Patent Application Laid-Open No. Hei-11-123185, and a device which computes the mastication iterations and the force of mastication (different from biting force and defined as a force by which food is crushed between upper and lower teeth, or by which upper and lower teeth are contacted together upon attaching an oral device such as a mouth piece where the muscle force exerted at every bite converges generally within 0.4 seconds) from the potential of the masticatory muscles using an electrode as disclosed in Japanese Patent Application Laid-Open No. 2001-178706.

SUMMARY OF THE INVENTION

However, there have been problems in that it is difficult to obtain accurate measurement results by conventional mastication monitoring devices because they are subjected to external factors.

The present invention has been carried out to solve the above problems, and the object of the present invention is to provide a mastication monitoring device by which accurate measurement results are readily obtainable.

In order to solve the above problems, the present mastication monitoring device is characterized in that a probe to be attached to a cheek which comprises a light source and a photodetector, and a mastication iteration counting means to count the mastication iterations based on time-series changes in at least one of the oxidized hemoglobin concentrations, the reduced hemoglobin concentrations and the oxygen saturation in the blood of the cheek, all of which are computed from the amount of light received by the photodetector, after a subject to be measured starts a series of mastication movements are provided.

Since the photodetector detects scattering light directly, there is little effect of external factors associated with the detection process of the scattering light. Accordingly, accurate time-series changes in the oxidized hemoglobin concentrations (the oxidized hemoglobin concentration in the blood), the reduced hemoglobin concentrations (the reduced hemoglobin concentration in the blood), and the oxygen saturation (the ratio of oxidized hemoglobin; $HbO_2/(HbO_2+Hb)$) can be computed from the amount of light received by the photodetector (the intensity of scattering light in the masticatory muscles detected by the photodetector). The mastication iteration counting means counts the mastication iterations based on the number of oscillation (time-series changes) of the oxidized hemoglobin concentrations, the reduced hemoglobin concentrations or the oxygen saturation, to readily obtain the accurate mastication iterations.

In order to solve the above problems, the present mastication monitoring device is characterized in that a probe to be attached to the cheek which comprises the light source and the photodetector, and a mastication force computing means to compute the force of mastication based on the time-series changes in at least one of the oxidized hemoglobin concentrations, the reduced hemoglobin concentrations and the oxygen saturation in the blood of the cheek, all of which are computed from the amount of light received by the photodetector, are provided.

The present invention utilizes a correlation between the amplitude (time-series changes) in the oxidized hemoglobin concentrations, the reduced hemoglobin concentrations and the oxygen saturation and the forces of mastication. It is possible to readily obtain accurate time-series changes in the forces of mastication, since the mastication force computing means computes mastication forces based on the time-series changes in the oxidized hemoglobin concentrations, the reduced hemoglobin concentrations or the oxygen saturation, all of which can be determined by the amount of light received by the photodetector.

The mastication monitoring device of the present invention is preferably provided further with a food hardness judging means to judge the hardness of food being masticated by a subject to be measured, based on the force of mastication computed by the mastication force computing means.

There is a correlation between the force of mastication and the hardness of food being masticated. Therefore, hardness of the food can be easily known by the food hardness judging means which judges hardness of food based on the force of mastication computed by the mastication force computing means.

The mastication monitoring device of the present invention is preferably provided further with a swallowability judging means which judges whether or not the food being masticated by a subject to be measured has become swallowable, based on the force of mastication computed by the mastication force computing means.

There is a correlation between the force of mastication and the hardness of food being masticated. Therefore, a swallowable state is judged by the swallowability judging means based on the force of mastication computed by the mastication force computing means such that swallowable state is judged when food becomes sufficiently soft.

In order to solve the above problems, the mastication monitoring device of the present invention is characterized in that a probe to be attached to the cheek which comprises the light source and the photodetector, and a mastication momentum computing means to compute the momentum of mastication after a subject to be measured starts a series of mastication movements, based on the time-series changes in at least one of the oxidized hemoglobin concentrations, the reduced hemoglobin concentrations and the oxygen saturation in the blood of the cheek, all of which are computed from the amount of light received by the photodetector, are provided.

An accurate momentum of mastication is readily obtainable by the mastication momentum computing means which computes the momentum of mastication based on the time-series changes in the oxidized hemoglobin concentrations, the reduced hemoglobin concentrations or the oxygen saturation, all of which are computed by the amount of light received by the photodetector.

The mastication monitoring device of the present invention is preferably provided further with a food viscosity judging means which judges the viscosity of the food being masticated by a subject to be measured, based on the momentum of mastication computed by the mastication momentum computing means.

There is a correlation between the momentum of mastication and the viscosity of the food being masticated. Therefore, the viscosity of food is readily known by the food viscosity judging means which judges the viscosity of food based on the momentum of mastication computed by the mastication momentum computing means.

In order to solve the above problems, the mastication monitoring device of the present invention is characterized in that two probes to be attached to the cheek which comprise the light source and the photodetector, and a mastication force balance computing means which computes an index showing a balance of bilateral mastication forces based on the time-series changes in at least one of the oxidized hemoglobin concentrations, the reduced hemoglobin concentrations and the oxygen saturation in the blood of the cheek, all of which are computed from the amount of light received by the photodetector of one probe as well as the time-series changes in at least one of the oxidized hemoglobin concentrations, the reduced hemoglobin concentrations and the oxygen saturation in the blood of the cheek, all of which are computed from the amount of light received by the photodetector of the other probe, are provided.

An accurate bilateral mastication force balance is readily obtainable by the mastication force balance computing means with the two probes which compute an index showing a balance of bilateral mastication forces based on the time-series changes in the oxidized hemoglobin concentrations, the reduced hemoglobin concentrations or the oxygen saturation, all of which are computed from the amount of light received by the respective photodetectors of each probe.

In order to solve the above problems, the mastication monitoring device of the present invention is characterized in that provided a probe to be attached to the cheek which comprises the light source and the photodetector, the mastication force computing means which computes the force of mastication based on the time-series changes in at least one of the oxidized hemoglobin concentrations, the reduced hemoglobin concentrations and the oxygen saturation in the blood of the cheek, all of which are computed from the amount of light received by the photodetector, the mastication momentum computing means to compute the momentum of mastication after a subject to be measured starts a series of mastication movements, based on the time-series changes in at least one of the oxidized hemoglobin concentrations, the reduced hemoglobin concentrations and the oxygen saturation in the blood of the cheek, all of which are computed from the amount of light received by the photodetector, a recording means to record the force of mastication computed by the mastication force computing means as well as the momentum of mastication computed by the mastication momentum computing means, and a mastication properness judging means to judge whether or not mastication is adequate by comparing the mastication force newly computed by the mastication force computing means with the past mastication force recorded on the recording means as well as comparing the mastication momentum newly computed by the mastication momentum computing means with the past mastication momentum recorded on the recording means, are provided.

When the mastication properness judging means judges properness of mastication for a specific food, properness or improperness of its mastication is readily and accurately known, since comparisons are made between the mastication force computed by the mastication force computing means and the past mastication force and between the mastication momentum computed by the mastication momentum computing means with the past mastication momentum.

BRIEF DESCRIPTION OF THE DRAWINGS

FIG. 15 shows time-series changes in the outputs S from the signal processing unit 3 (time-series changes in the oxygen saturation).

DESCRIPTION OF THE PREFERRED EMBODIMENTS

Figure 1:
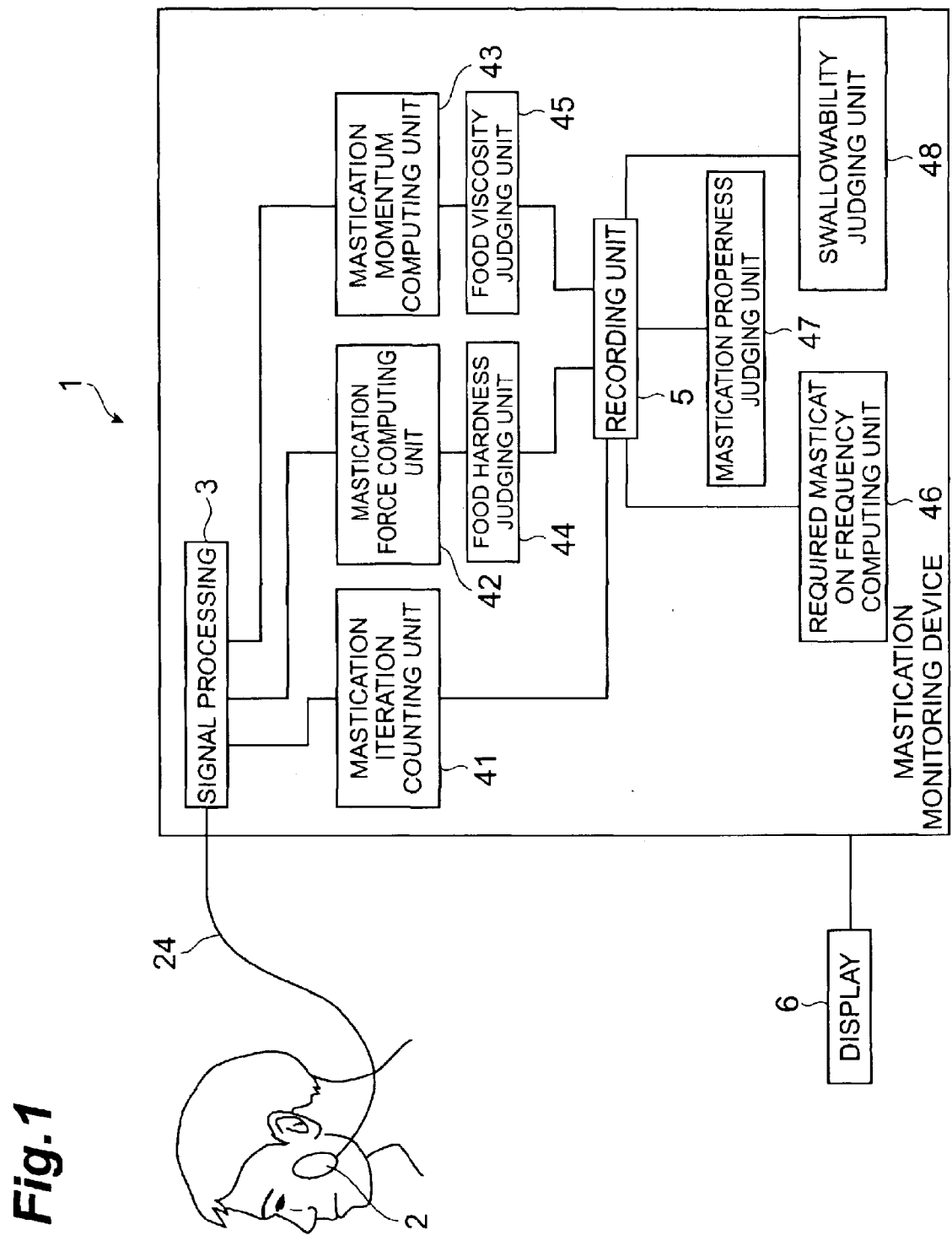
FIG. 1 shows the functional configuration of a mastication monitoring device 1.

Preferred embodiments of the mastication monitoring device of the present invention will be described hereinafter with reference to the accompanying drawings. It should be noted that the same components in the drawings are designated the same reference numerals and overlapping explanations are omitted.

(First Embodiment)

Figure 2:
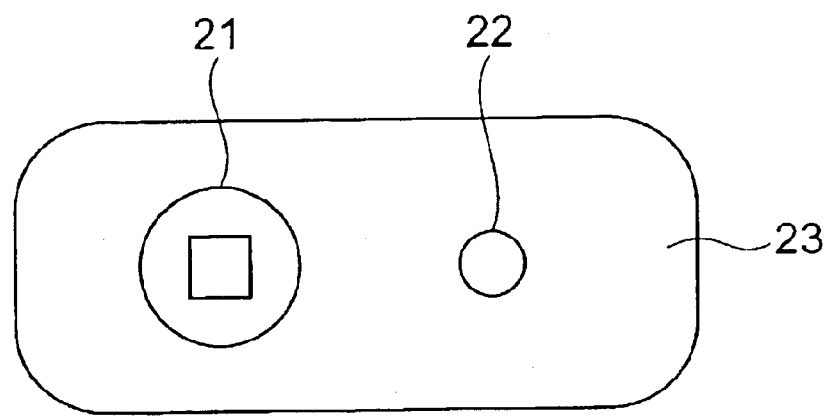
FIG. 2 shows the front view of a probe 2.

First, the functional configuration of mastication monitoring device 1 according to a first embodiment of the present invention will be explained. FIG. 1 is a diagram showing the functional configuration of the mastication monitoring device 1. The mastication monitoring device 1 is provided with probe 2 which is attached to the cheek in order to detect the oxidized hemoglobin concentration, the reduced hemoglobin concentration and the oxygen saturation in the masticatory muscles (masseter muscle, temporal muscle, etc.). As shown in FIG. 2, the probe 2 is provided with light source 21 to irradiate the masticatory muscles with light, photodetector 22 to detect scattering light scattered in the masticatory muscles when irradiated, and tabular holder 23 to hold these parts. The holder 23 is made of elastic silicone rubber. On its surface are arranged the light source 21 and the photodetector 22 with an interspace of several centimeters and the holder is made attachable to the skin with adhesive tape. The specific wavelength components of the light emitted from the light source 21 are absorbed by the oxidized hemoglobin and the reduced hemoglobin contained in the blood of the masticatory muscles and the light is scattered in the masticatory muscles at the same time. The scattered light is detected by the photodetector 22, and a signal of the amount of light received is transmitted, via cable 24, to signal processing unit 3 described below.

As shown in FIG. 1, the main body of the mastication monitoring device 1 is provided, as the functional elements, with the signal processing unit 3 to control the light source 21 as well as to receive the above signal of the amount of light received and carry out a predetermined computing process, mastication iteration counting unit 41 which counts the mastication iterations after starting a series of mastication movements, based on the information delivered from the signal processing unit 3, mastication force computing unit 42 which computes the force of mastication based on the information delivered from the signal processing unit 3, mastication momentum computing unit 43 which computes the momentum of mastication after starting a series of mastication movements, based on the information delivered from the signal processing unit 3, food hardness judging unit 44 which judges hardness of food based on the information delivered from the mastication force computing unit 42, food viscosity judging unit 45 which judges viscosity of food based on the information delivered from the mastication momentum computing unit 43, required mastication iteration computing unit 46 which computes a required iteration (number) for mastication based on both the food hardness and the food viscosity, mastication properness judging unit 47 which judges whether or not mastication is adequate by comparing the present information with the past information with respect to both the mastication forces and the mastication momentums, swallowability judging unit 48 which judges swallowable conditions based on the information (mastication force) delivered from the mastication force computing unit 42 and recording unit 5. The mastication monitoring device 1 is also provided with display 6 which displays the results of measurement or judgment carried out by each unit of the main body of the mastication monitoring device 1.

Next, operation to compute the mastication iterations by the mastication iteration counting unit 41 will be explained.

Figure 3:
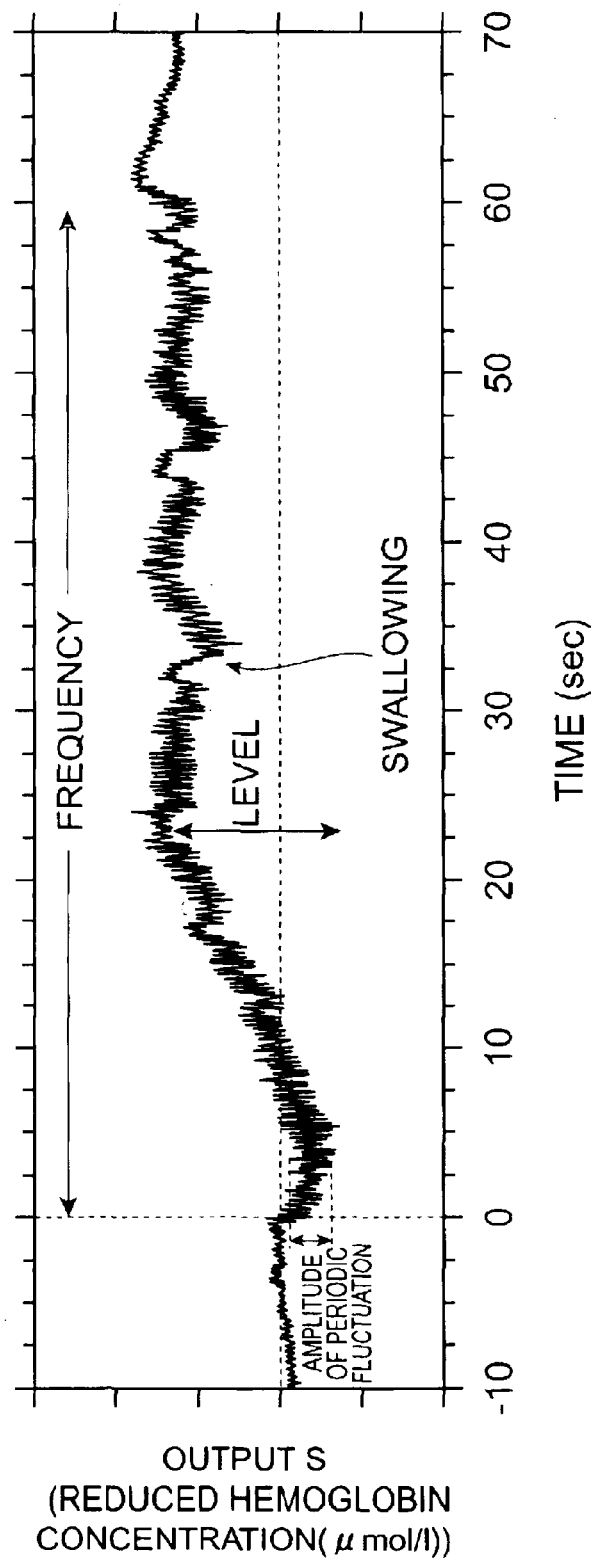
FIG. 3 shows time-series changes in outputs S from a signal processing unit 3 (time-series changes in the reduced hemoglobin concentrations).

FIG. 3 shows time-series changes in the outputs S from the signal processing unit 3 (time-series changes in the reduced hemoglobin concentrations) when peanuts are masticated for one minute as an example. In this embodiment, the signal processing unit 3 produces outputs equivalent to the reduced hemoglobin concentrations. The signal processing unit 3 computes the reduced hemoglobin concentrations (time-series changes) from signals of the amounts of light received by the photodetector 22, followed by computation of the output S (time-series changes) corresponding to the time-series changes in the reduced hemoglobin concentrations. The present inventors discovered from their experiments that there is a correlation between the amplitude of the oxidized hemoglobin concentration, the reduced hemoglobin concentration or the saturated oxygen concentration and the force of mastication. Namely, the output S represents the level of the mastication force.

As mastication movement is initiated and a rise in the output level of the signal processing unit 3 is followed, periodic fluctuations corresponding to the mastication cycles are observed. When mastication movement is suspended to swallow crushed food, these periodic fluctuations corresponding to the mastication cycles disappear. When mastication movement is terminated, the output level of the signal processing unit 3 is reduced (or the periodic fluctuations stop). The mastication iteration counting unit 41 counts the mastication iterations after starting a series of mastication movements from these periodic fluctuations. The mastication iteration counting unit 41 computes the moving average value Sma of the outputs S periodically. This period is adjusted to the average length of one cycle of mastication. In addition, the mastication iteration counting unit 41 extracts the output S(n) in a period shorter than the average length of one cycle of mastication, and then computes Sd(n) by subtracting the moving average value Sma from the output S (n) Namely, Sd(n) is represented by the following equation (1). It should be noted that processing of subtracting the moving average value Sma is intended to exclude an effect due to changes in exerted muscle force having a period longer than mastication.

$$Sd(n)=S(n)-Sma \quad (1)$$

where n represents the number of extractions of the output S after the mastication iteration counting unit 41 starts counting.

Figure 4:
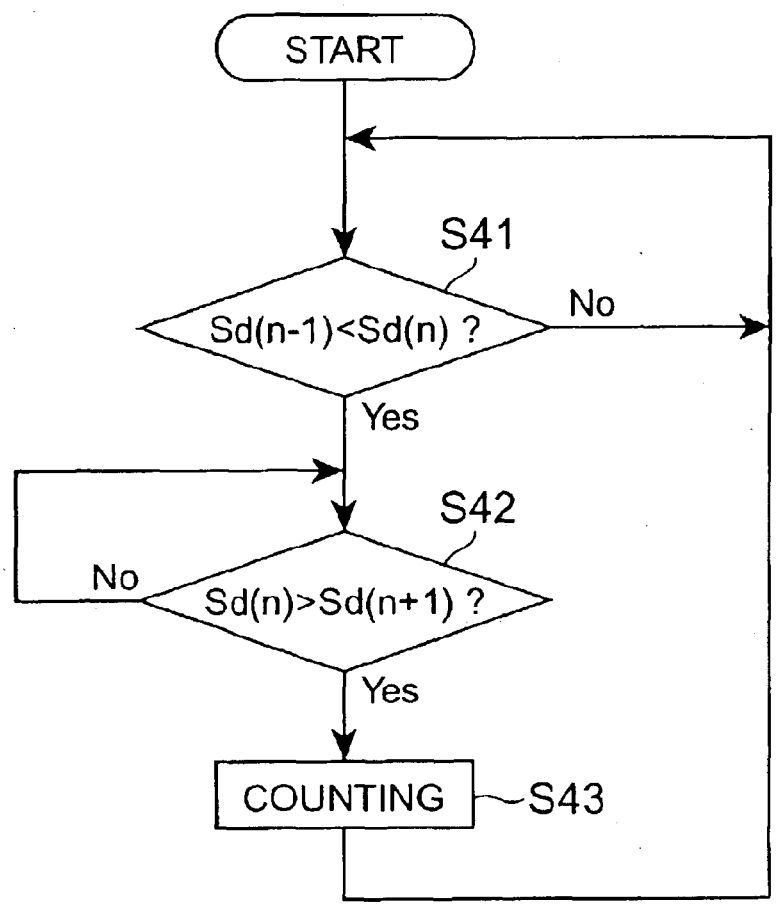
FIG. 4 is a flowchart showing operations to detect a peak of Sd and count the mastication iterations by a mastication iteration counting unit 41

FIG. 4 is a flowchart showing operations to detect peaks of Sd and count the mastication iterations by the mastication iteration counting unit 41. The mastication iteration counting unit 41 judges whether Sd (n) is larger than Sd(n−1) (S41). If Sd(n) is smaller than or equal to Sd(n−1), S41 is repeated in the next number of extraction.

If Sd(n) is larger than Sd(n−1) in S41, the mastication iteration counting unit 41 judges whether Sd(n) is larger than Sd(n+1) (S42). If Sd(n) is smaller than Sd(n+1) or equal to Sd(n+1), S42 is repeated in the next number of extraction.

If Sd(n) is larger than Sd(n+1) in S42, Sd(n) is judged to be a peak and counted as a mastication iteration (S43). However, if the peak of Sd is not separated from the previous peak of Sd by the predetermined number of extractions, it is judged not to be a periodic fluctuation of Sd due to mastication and is not counted. The mastication iteration counting unit 41 counts the mastication iterations by repeating the above processes. It should be noted that the above processes detect the crest peak of the periodic fluctuations in Sd, while mastication iteration may also be counted by detecting the trough peak.

Figure 12:
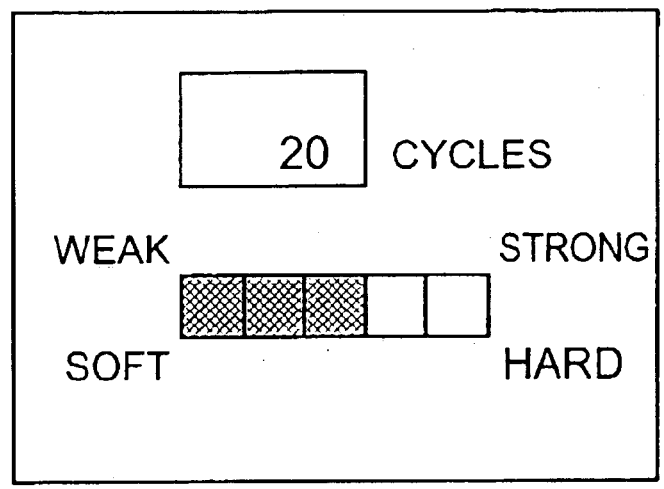
FIG. 12 shows an example of the display of the mastication iterations after starting a series of mastication movements and the mastication force (a five scale rating) on a display 6.

Next, operations to compute the force of mastication by the mastication force computing unit 42 and to judge the hardness of food being masticated by the food hardness judging unit 44 will be explained. The mastication force computing unit 42 computes the force of mastication from the amplitude of the output S. To be more specific, the difference Sp between the crest of Sd (peak) and the immediately preceding trough of Sd is computed and its sequential values are moving-averaged, thereby allowing computation of the mastication force Smap. Here, the computation of the moving average is intended to correct variation in mastication forces in a short period. If the crest of Sd (peak) is not separated from the immediately preceding trough of Sd by the predetermined number of extraction, it is judged not to be a periodic fluctuation of Sd due to mastication and is excluded from the computation of the moving average. The computed mastication forces may be displayed on the display 6 by classifying according to the differences in strength. FIG. 12 shows an example of the display of mastication iterations (cycles) after starting a series of mastication movements and mastication force on the display 6. In this way, fine changes in mastication forces can be traced by computing the force of mastication from the amplitude of the output S.

Figure 5:
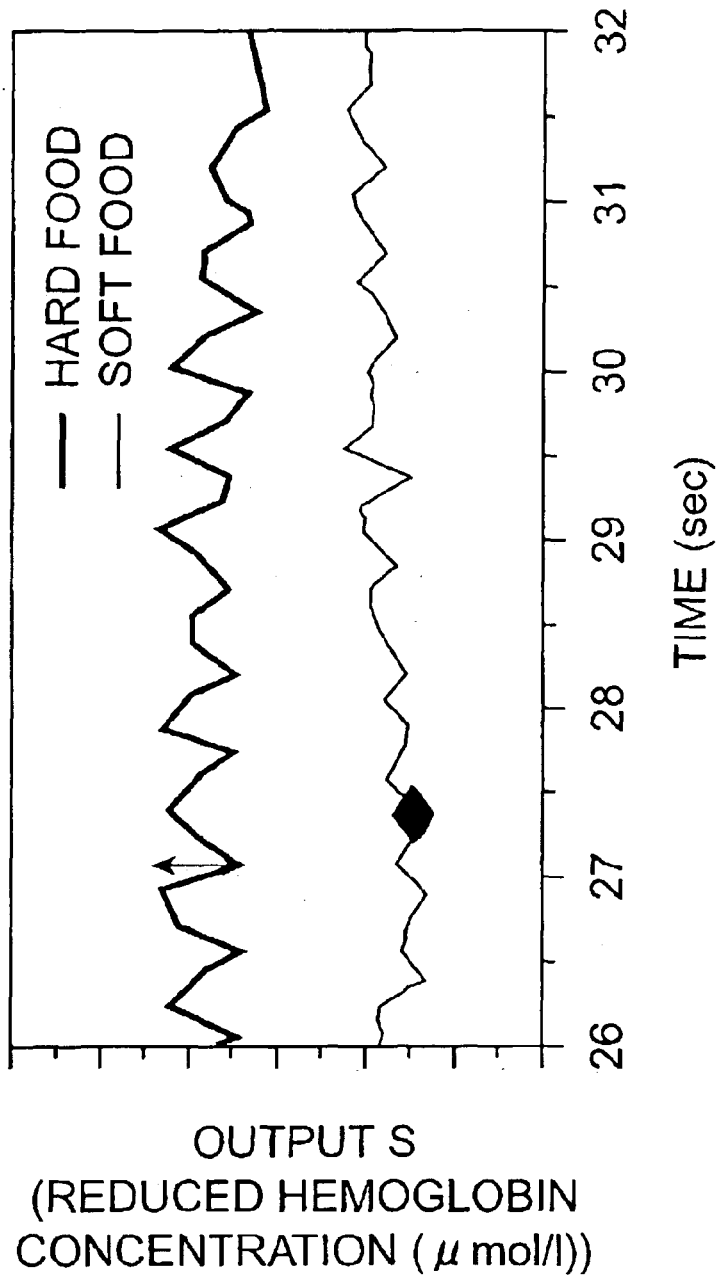
FIG. 5 shows time-series changes in the outputs S from the signal processing unit 3 (time-series changes in the reduced hemoglobin concentrations) when hard food and soft food are being masticated, respectively.

FIG. 5 shows time-series changes in the outputs S from the signal processing unit 3 (time-series changes in the reduced hemoglobin concentrations) when peanuts are masticated as an example of hard food and jelly is masticated as an example of soft food. As shown in FIG. 5, the level of the output S becomes higher and the amplitude of the output S becomes larger when food being masticated is hard. In other words, there is a correlation between the hardness of food being masticated and the force of mastication. The food hardness judging unit 44 judges the hardness of food from the data on mastication force delivered from the mastication force computing unit 42 and the data on the correlation between the magnitude of mastication force and the hardness of food stored in the recording unit 5.

Next, operations to compute the momentums of mastication by the mastication momentum computing unit 43 and to judge the viscosity of food by the food viscosity judging unit 45 will be explained. The mastication momentum [N·s] is obtained by integrating the level of muscle forces exerted by the masticatory muscles with respect to time. The mastication momentum computing unit 43 computes the momentum of mastication by integrating the level of the output S after starting a series of mastication movements (when the output S started oscillating) with respect to time.

Figure 6:
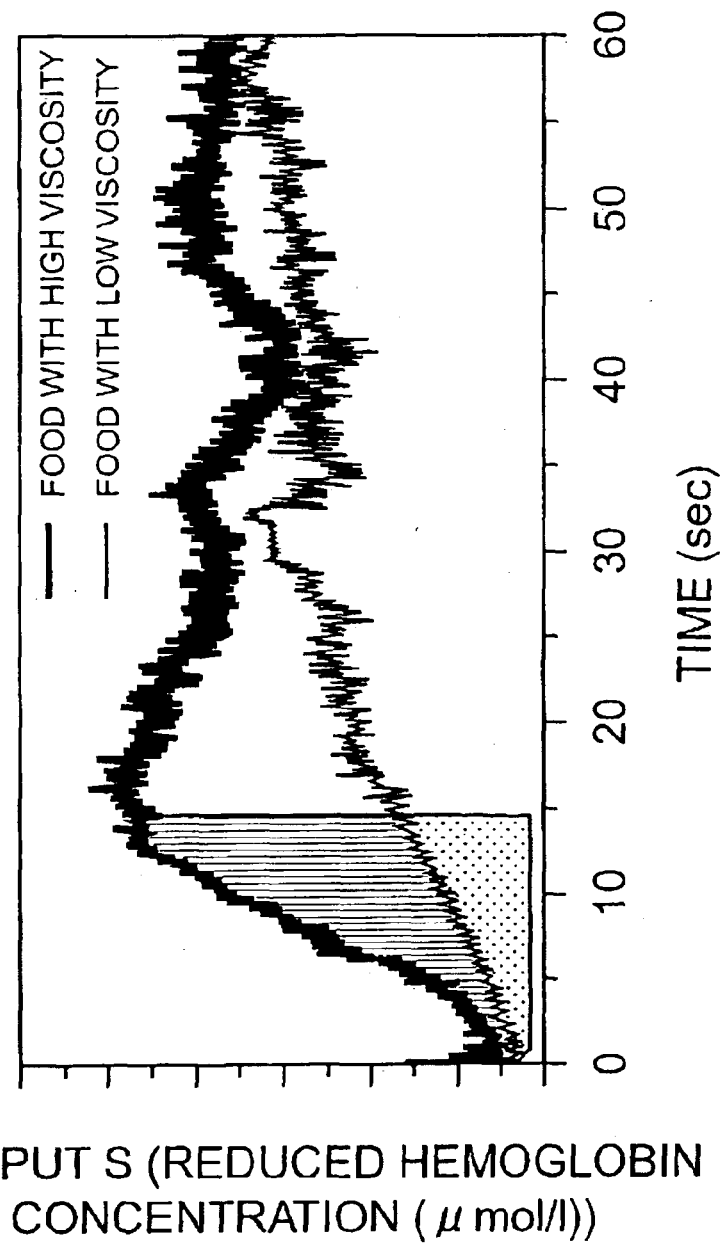
FIG. 6 shows time-series changes in the outputs S from the signal processing unit 3 (time-series changes in the reduced hemoglobin concentrations) when foods with a high viscosity and a low viscosity are being masticated, respectively.

FIG. 6 shows time-series changes in the outputs S from the signal processing unit 3 (time-series changes in the reduced hemoglobin concentrations) when chewing gum is masticated as an example of food with a high viscosity and jelly is masticated as an example of food with a low viscosity. As shown in FIG. 6, the momentum of mastication after starting mastication movements becomes large when the viscosity of food being masticated is high. In other words, there is a correlation between the momentum of mastication and the viscosity of food. The food viscosity judging unit 45 judges the viscosity of food from the data on mastication momentum delivered from the mastication momentum computing unit 43 and the data on the correlation between the magnitude of mastication momentum after starting a series of mastication movements and the viscosity of food stored in the recording unit 5.

Figure 7:
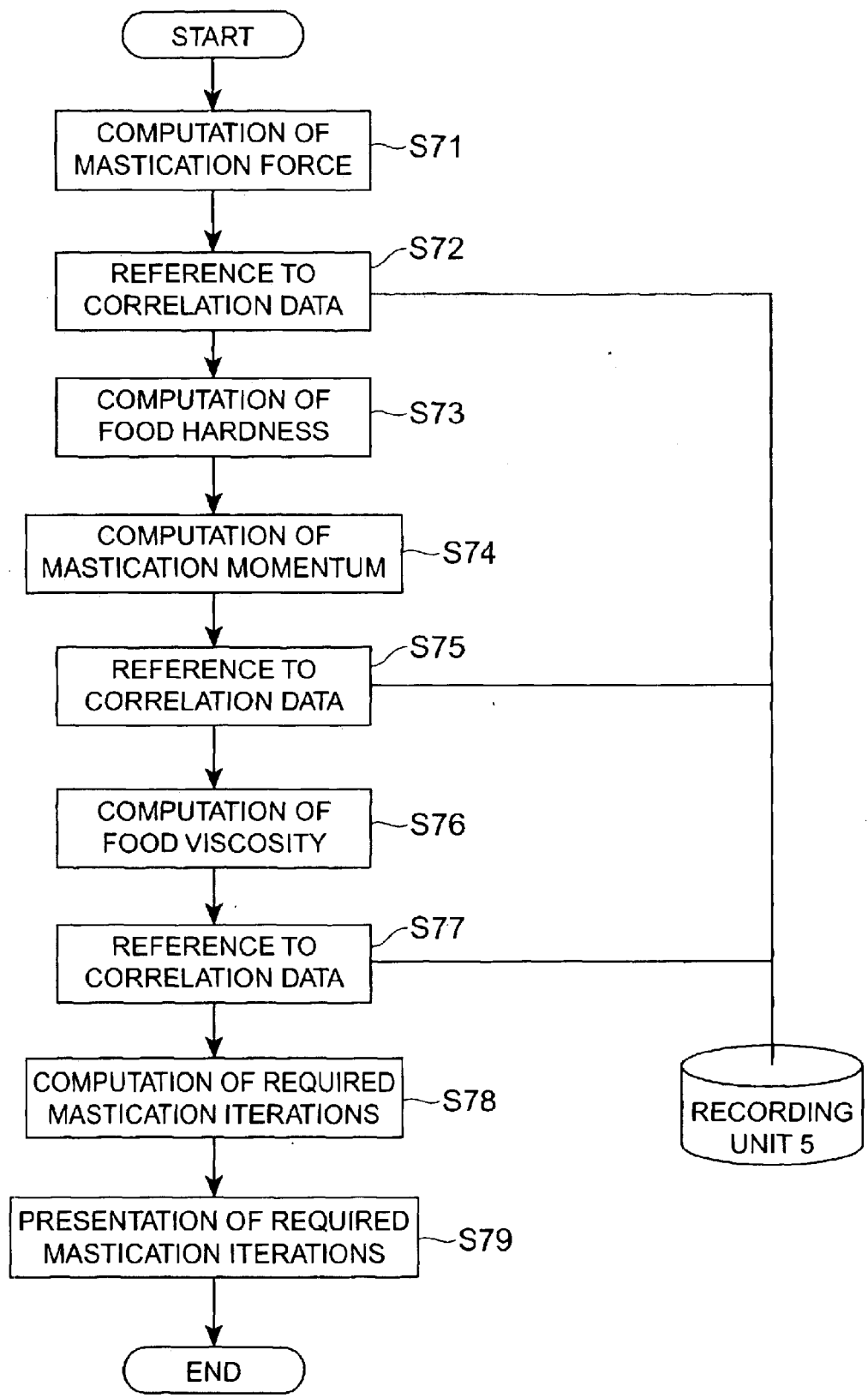
FIG. 7 is a flowchart showing the operational procedures to count required mastication iterations by the mastication monitoring device 1.

Following a series of operations by the mastication force computing unit 42, the food hardness judging unit 44, the mastication momentum computing unit 43 and the food viscosity judging unit 45, operations to compute the mastication iterations necessary for swallowing by the required mastication iteration computing unit 46 will be explained below. FIG. 7 is a flowchart showing the operational procedures to compute the required mastication iterations by the mastication monitoring device 1.

The mastication force computing unit 42 computes mastication forces from the amplitude of the output S (S71).

The food hardness judging unit 44 refers to the data on the correlation between the strength of the force of mastication and the hardness of food (S72).

The food hardness judging unit 44 computes the hardness of food (S73).

The mastication momentum computing unit 43 computes the momentum of mastication after starting mastication movements by integrating the level of the output S with respect to time (S74).

The food viscosity judging unit 45 refers to the data on the correlation between the magnitude of the momentum of mastication and the hardness of food (S75).

The food viscosity judging unit 45 computes the viscosity of food (S76).

The required mastication iteration computing unit 46 refers to the data on the correlation between the hardness and the viscosity of food and the required mastication iterations (S77), and computes the mastication iterations necessary for swallowing the aforementioned food (S78).

The display 6 presents the required mastication iterations (S79).

Figure 8:
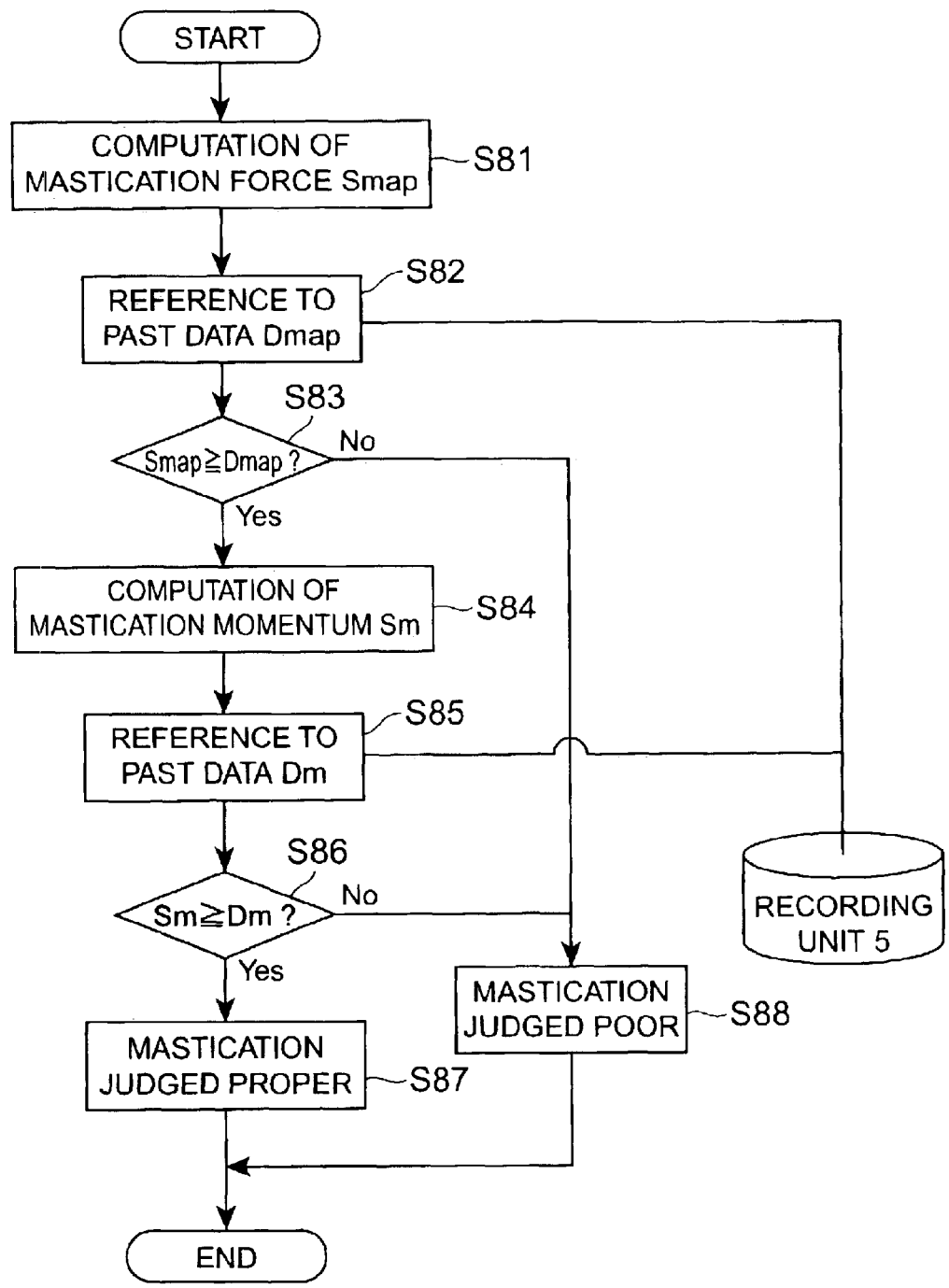
FIG. 8 shows the operational procedures to judge properness of mastication by a mastication properness judging unit 47.

Next, operations to judge properness of mastication by the mastication properness judging unit 47 will be explained. FIG. 8 shows the operational procedures for judging properness of mastication by the mastication properness judging unit 47. The mastication force computing unit 42 computes the mastication force Smap from the amplitude of the output S (S81).

The mastication properness judging unit 47 refers to the mastication forces Dmap (past data) which are recorded in the recording unit 5 when the same food is masticated in the past (S82), and the mastication force Smap and the mastication force Dmap are compared (S83). When the mastication force Smap is smaller than the mastication force Dmap, the mastication properness judging unit 47 judges that the mastication is poor (S88).

When the mastication force Smap is larger than or equal to the mastication force Dmap, the mastication momentum computing unit 43 computes the mastication momentum Sm from the beginning to the end of the mastication movements (S84).

The mastication properness judging unit 47 refers to the mastication momentums Dm (past data) which are recorded in the recording unit 5 when the same food is masticated in the past (S85), and the mastication momentum Sm and the mastication momentum Dm are compared (S86). When the mastication momentum Sm is smaller than the mastication momentum Dm, the mastication properness judging unit 47 judges that the mastication is poor (S88).

When the mastication momentum Sm is larger than or equal to the mastication momentum Dm, the mastication properness judging unit 47 judges that the mastication is good (S87). It is possible to know daily mastication properness by the above processes.

Figure 9:
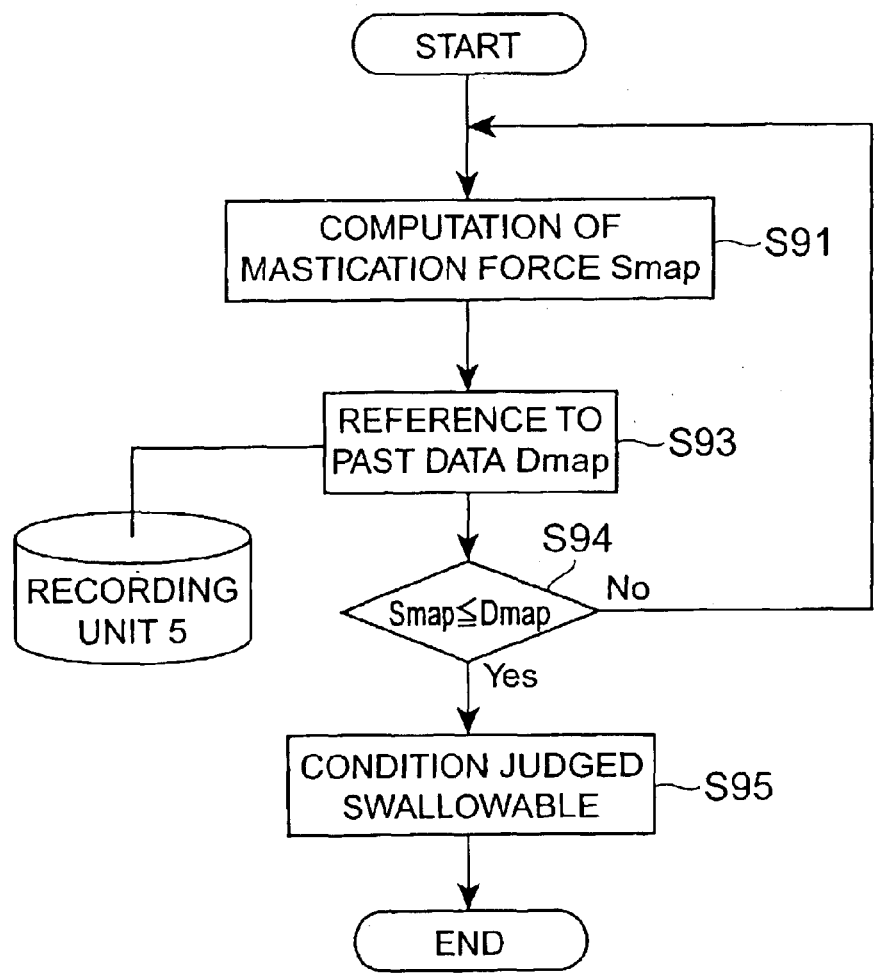
FIG. 9 is a flowchart showing the operational procedures to judge swallowable conditions by a swallowability judging unit 48.

Next, operations to judge swallowable conditions by the swallowability judging unit 48 will be explained. FIG. 9 is a flowchart showing the operational procedures for judging swallowable conditions by the swallowability judging unit 48. The mastication force computing unit 42 computes the mastication force Smap from the amplitude of the output S (S91).

The swallowability judging unit 48 refers to the mastication forces Dmap (past data) which are stored in the recording unit 5 when the same food is swallowed in the past (S93), and the mastication force Smap and the mastication force Dmap are compared (S94). When the mastication force Smap is larger than the mastication force Dmap, the swallowability judging unit 48 judges that the food is not sufficiently crushed, returning to the process of S91.

When the mastication force Smap is smaller than or equal to the mastication force Dmap, the swallowability judging unit 48 judges that the food has been sufficiently crushed and is in swallowable condition (S95). Since there is a correlation between the mastication force Smap and the hardness of the food being masticated as described above, swallowable conditions may be judged by the above processes when the food has become softer than the same food swallowed in the past.

(Second Embodiment)

Figure 10:
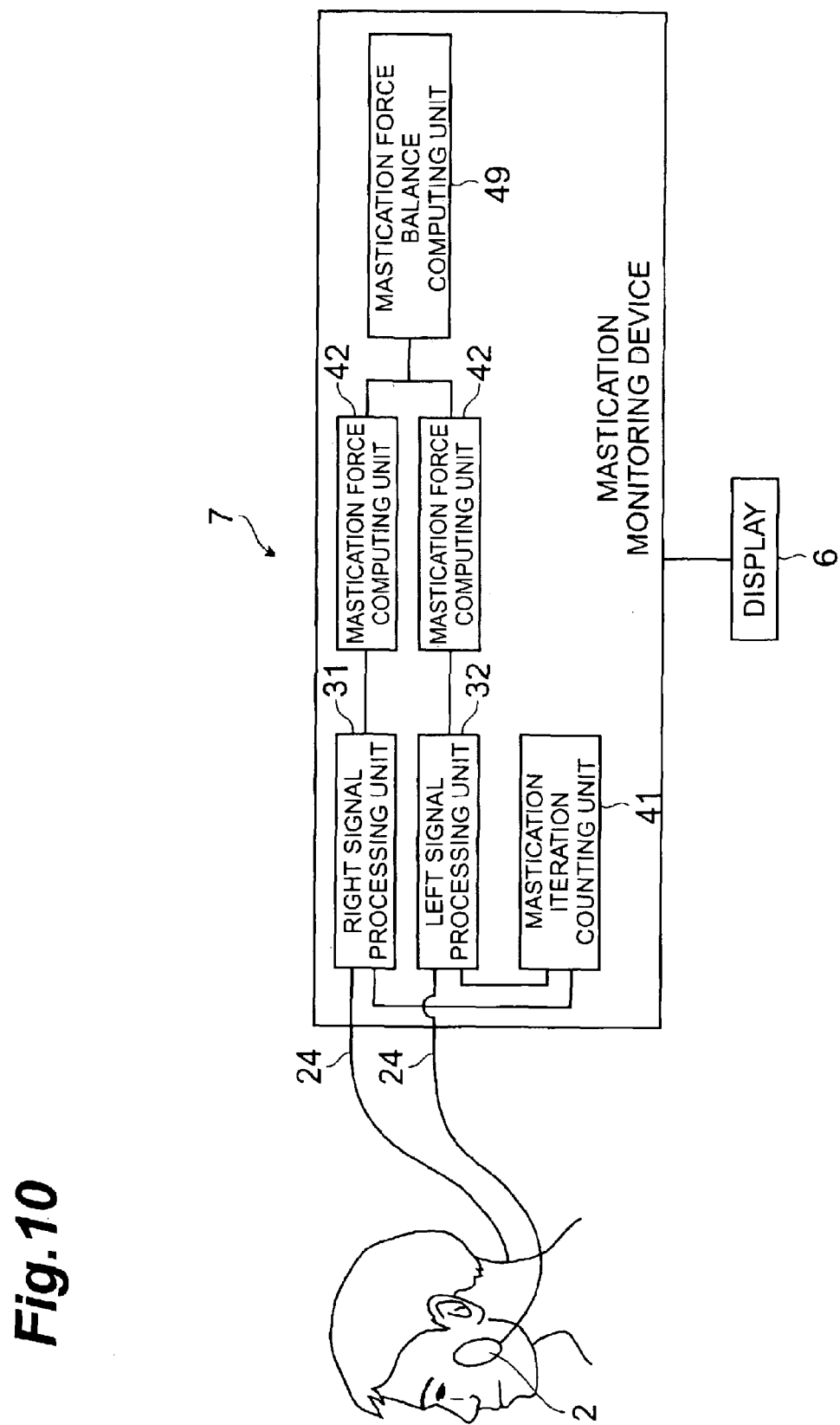
FIG. 10 shows the functional configuration of a mastication monitoring device 7.

First of all, the functional configuration of mastication monitoring device 7 according to a second embodiment of the present invention will be explained. FIG. 10 is a diagram showing the functional configuration of the mastication monitoring device 7. The mastication monitoring device 7 is provided with two probes 2 (probe 2 for the right cheek and probe 2 for the left cheek). The two probes 2 are attached to the right and left cheeks, respectively, and connected to right signal processing unit 31 and left signal processing unit 32 of the main body of the mastication monitoring device 7 via cables 24, respectively.

As shown in FIG. 10, the main body of the mastication monitoring device 7 is provided, as the functional components, with the right signal processing unit 31 and the left signal processing unit 32 to control the light source 21 as well as to receive a signal of the amount of light received from the probe 2 and to carry out a predetermined computing process, mastication iteration counting unit 41 which counts the mastication iterations during a series of mastication movements based on the information delivered from the right signal processing unit 31 and the left signal processing unit 32, mastication force computing units 42 which compute the force of mastication based on the information delivered from the right signal processing unit 31 and the left signal processing unit 32, and mastication force balance computing unit 49 which computes an index showing a balance of bilateral mastication forces based on the bilateral mastication forces computed by the mastication force computing units 42. The mastication monitoring device 7 is also provided with display 6 which displays the results of measurement and judgment carried out by each unit of the main body of the mastication monitoring device 7.

Next, operations to compute an index showing a balance of bilateral mastication forces by the mastication force balance computing unit 49 will be explained. The right signal processing unit 31 computes the reduced hemoglobin concentrations (time-series changes) from the signal of the amount of light received by the photodetector 22 on the probe 2 for the right cheek and further computes the output Sr corresponding to the time-series changes in the reduced hemoglobin concentrations. In a similar way, the left signal processing unit 32 computes the output Sl based on the signal of the amount of light received by the photodetector 22 on the probe 2 for the left cheek. The output Sr and the output Sl are delivered to the mastication iteration counting unit 41 and the mastication force balance computing unit 49.

The mastication iteration counting unit 41 counts the mastication iterations after starting a series of mastication movements in procedures similar to those in the first embodiment.

The two mastication force computing units 42 compute the right and left mastication forces, respectively, in procedures similar to those in the first embodiment.

The mastication force balance computing unit 49 computes Srn by subtracting the value of output Sr at the beginning of a series of mastication movements from a value of output Sr newly obtained. The mastication force balance computing unit 49 computes Sln by subtracting the value of output Sl at the beginning of a series of mastication movements from a value of output Sl newly obtained.

Subsequently, the mastication force balance computing unit 49 computes Bl represented by the following equation (2). Bl is an index showing an unbalance towards the right mastication force in the balance of bilateral mastication forces. When Bl exceeds 0.5, it implies that the right cheek is being used more strongly. When Bl falls below 0.5, it implies that the left cheek is being used more strongly.

$$Bl=Srn/(Srn+Sln) \qquad (2)$$

Figure 13:
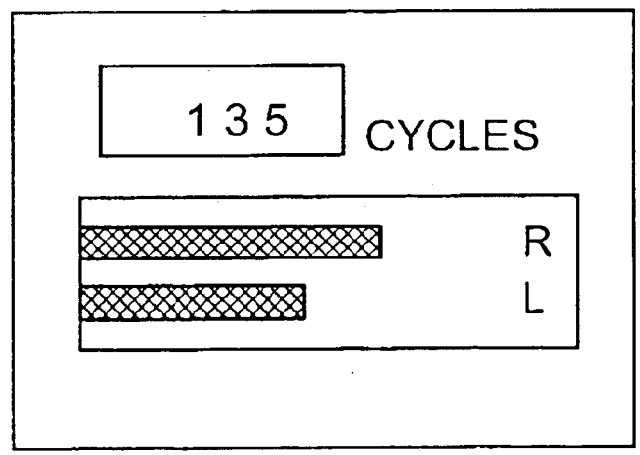
FIG. 13 shows an example of the display of the mastication iterations after starting a series of mastication movements and the bilateral mastication forces on the display 6.

The mastication iterations counted by the mastication iteration counting unit 41 and the Bl computed by the mastication force balance computing unit 49 are displayed on the display 6. FIG. 13 shows an example displaying the mastication iterations (cycles) and the bilateral mastication forces after starting a series of mastication movements.

Figure 11:
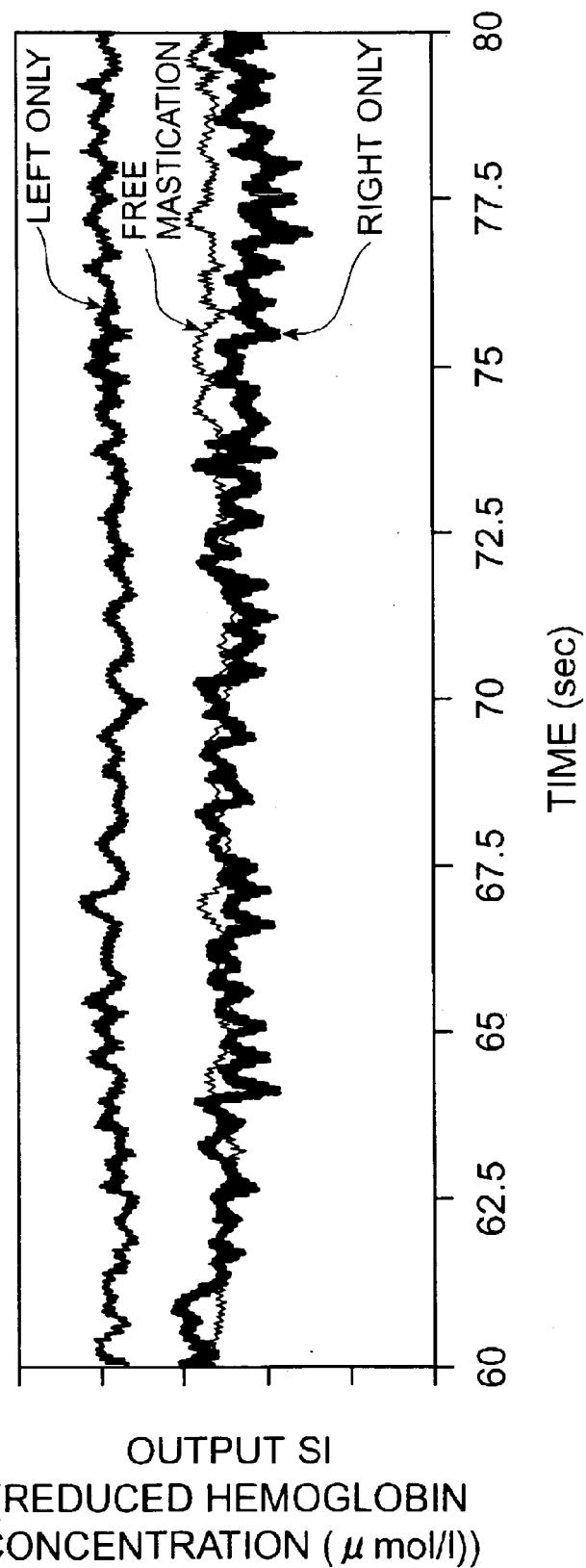
FIG. 11 shows time-series changes in the outputs S1 from a left signal processing unit 32 (time-series changes in the reduced hemoglobin concentrations) when chewing gum is masticated on the right side, on the left side or freely.

FIG. 11 shows time-series changes in the outputs Sl from the left signal processing unit 32 (time-series changes in the reduced hemoglobin concentrations) when chewing gum was masticated on the right side, on the left side or freely. As shown in FIG. 11, the mastication force in the left cheek is stronger in the case where the subject of measurement masticates chewing gum on the left side, compared to the case where the subject masticates chewing gum on the right side. In the case where the subject masticates freely, the mastication force in the left cheek is close to that in the case where the subject masticates on the right side. Hence, it is known that the subject of measurement is in the habit of masticating mainly on the right side when masticating freely. Accordingly, it is also possible to know the habit of a subject as to which side is used in free mastication by presenting the time-series changes in the outputs from one signal processing unit.

According to the above embodiment, accurate mastication iterations, mastication force, mastication momentum and the like can be readily obtained by utilizing the outputs S (time-series changes) computed in response to the time-series changes in the reduced hemoglobin concentrations.

In addition, the probe 2 is easy to handle since it is a simple device composed of the light source 21 and the photodetector 22. The display 6 may be integrated with the probe 2.

In the above embodiment, the signal processing unit detects the reduced hemoglobin concentration. However the oxidized hemoglobin concentration or the oxygen saturation ($HbO_2/(HbO_2+Hb)$), instead of the reduced hemoglobin concentration, may be detected by a signal processing unit and be used for computing mastication iterations, mastication force, mastication momentum and the like.

Figure 14:
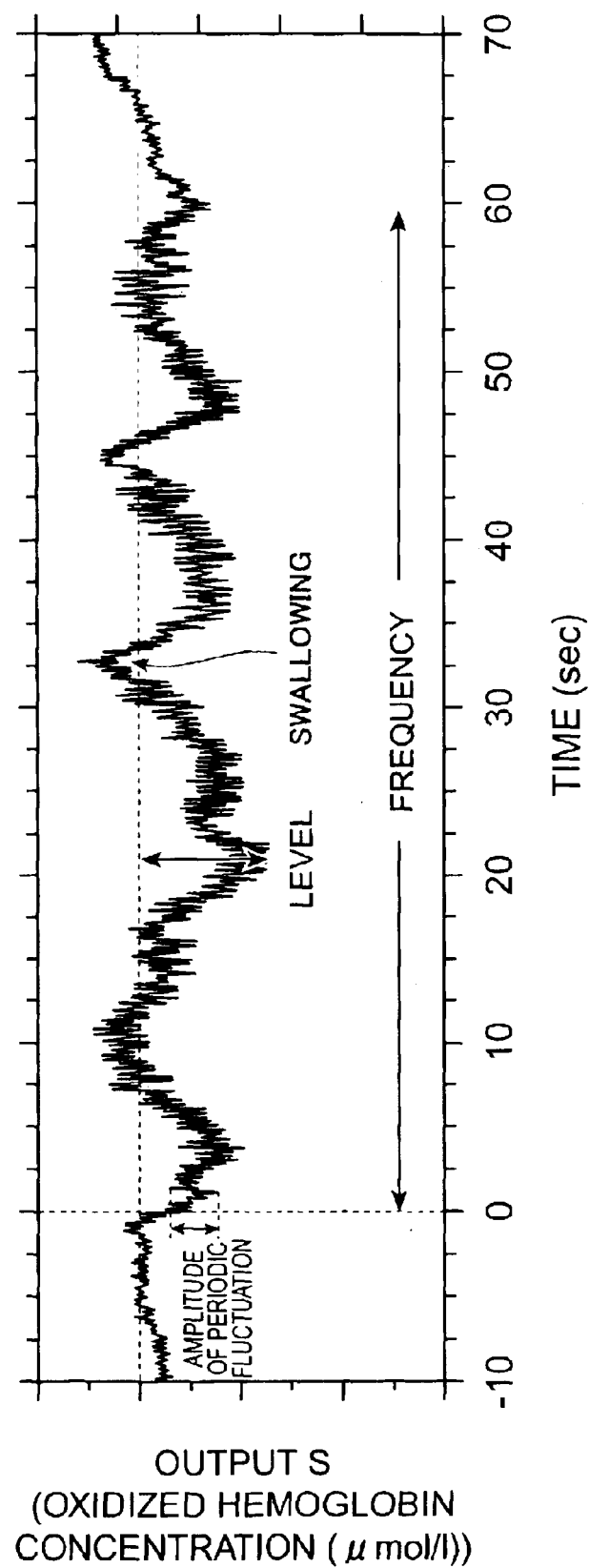
FIG. 14 shows time-series changes in the outputs S from the signal processing unit 3 (time-series changes in the oxidized hemoglobin concentrations).

FIG. 14 shows time-series changes in the outputs S when the outputs S are equivalent to the oxidized hemoglobin concentrations. It should be noted that the measurement conditions are the same as those in the example described in FIG. 3 where peanuts are masticated for one minute. Since periodic fluctuations in the outputs S corresponding to the mastication movements are observed in this instance as well, it is possible to obtain the mastication iterations, the mastication force and the like by the same method and device as those in the above embodiment where the time-series changes in the reduced hemoglobin concentrations are used.

FIG. 15 shows time-series changes in the outputs S when the outputs S are equivalent to the oxygen saturation. It should be noted that the measurement conditions are the same as those in the example described in FIG. 3 where peanuts are masticated for one minute. Since periodic fluctuations in the outputs S corresponding to the mastication movements are observed in this instance as well, it is possible to obtain the mastication iterations, the mastication force, the mastication momentum and the like by the same method and device as those in the above embodiment where the time-series changes in the reduced hemoglobin concentrations are used.

What is claimed is:

1. A mastication monitoring device comprising:
   a probe to be attached to a cheek, comprising a light source and a photodetector; and
   a mastication iteration counting means to count the mastication iterations after a subject to be measured starts a series of mastication movements, based on time-series changes in at least one of the oxidized hemoglobin concentrations, the reduced hemoglobin concentrations and the oxygen saturation in the blood of said cheek, each computed from the amount of light received by said photodetector.

2. A mastication monitoring device comprising:
   a probe to be attached to a cheek, comprising a light source and a photodetector; and
   a mastication force computing means to compute the force of mastication, based on time-series changes in at least one of the oxidized hemoglobin concentrations, the reduced hemoglobin concentrations and the oxygen saturation in the blood of said cheek, each computed from the amount of light received by said photodetector.

3. The mastication monitoring device according to claim 2, further comprising a food hardness judging means to judge the hardness of the food being masticated by a subject to be measured, based on the force of mastication computed by said mastication force computing means.

4. The mastication monitoring device according to claim 2, further comprising a swallowability judging means to judge whether or not the food being masticated by a subject to be measured has become swallowable, based on the force of mastication computed by said mastication force computing means.

5. A mastication monitoring device comprising:
   a probe to be attached to a cheek, comprising a light source and a photodetector; and
   a mastication momentum computing means to compute the momentum of mastication after a subject to be measured starts a series of mastication movements, based on time-series changes in at least one of the oxidized hemoglobin concentrations, the reduced hemoglobin concentrations and the oxygen saturation in the blood of said cheek, each computed from the amount of light received by said photodetector.

6. The mastication monitoring device according to claim 5, further comprising a food viscosity judging means to judge viscosity of the food being masticated by the subject to be measured, based on the momentum of mastication computed by said mastication momentum computing means.

7. A mastication monitoring device comprising:
   two probes to be attached to the cheeks, each comprising a light source and a photodetector; and
   a mastication force balance computing means which computes an index showing a balance of bilateral mastication forces, based on time-series changes in at least one of the oxidized hemoglobin concentrations, the reduced hemoglobin concentrations and the oxygen saturation in the blood of said cheek, each computed from the amount of light received by said photodetector of one probe, and time-series changes in at least one of the oxidized hemoglobin concentrations, the reduced hemoglobin concentrations and the oxygen saturation in the blood of said cheek, each computed from the amount of light received by said photodetector of the other probe.

8. A mastication monitoring device comprising:
   a probe to be attached to a cheek, comprising a light source and a photodetector;
   a mastication force computing means to compute the force of mastication, based on time-series changes in at least one of the oxidized hemoglobin concentrations, the reduced hemoglobin concentrations and the oxygen saturation in the blood of said cheek, each computed from the amount of light received by said photodetector;
   a mastication momentum computing means to compute the momentum of mastication after a subject to be measured starts a series of mastication movements, based on time-series changes in at least one of the oxidized hemoglobin concentrations, the reduced hemoglobin concentrations and the oxygen saturation in the blood of said cheek, each computed from the amount of light received by said photodetector;
   a recording means to record the force of mastication computed by said mastication force computing means and the momentum of mastication computed by said mastication momentum computing means; and
   a mastication properness judging means to judge whether or not mastication is adequate by comparing the mastication force newly computed by said mastication force computing means with the past mastication force recorded on said recording means as well as comparing the mastication momentum newly computed by said mastication momentum computing means with the past mastication momentum recorded on said recording means.

* * * * *